US00PP24344P3

(12) United States Plant Patent
Bourne

(10) Patent No.: US PP24,344 P3
(45) Date of Patent: Mar. 25, 2014

(54) ***DIANTHUS* PLANT NAMED 'WP10 ELE04'**

(50) Latin Name: *Dianthus×hybrida*
Varietal Denomination: WP10 ELE04

(76) Inventor: Carolyn Grace Bourne, Dawlish (GB)

( * ) Notice: Subject to any disclaimer, the term of this patent is extended or adjusted under 35 U.S.C. 154(b) by 435 days.

(21) Appl. No.: 13/134,345

(22) Filed: Jun. 6, 2011

(65) Prior Publication Data

US 2011/0321207 P1 Dec. 29, 2011

(51) Int. Cl.
*A01H 5/00* (2006.01)

(52) U.S. Cl.
USPC ..... Plt./281; Plt./272

(58) Field of Classification Search
USPC ..... Plt./281, 272
See application file for complete search history.

*Primary Examiner* — June Hwu
*Assistant Examiner* — Louanne Krawczewicz Myers

(57) ABSTRACT

A new cultivar of *Dianthus* plant named 'WP10 ELE04' which is characterized by compact mounding habit, glaucous, blue green foliage and fragrant double light shell pink flowers. In combination, these characteristics set 'WP10 ELE04' apart from all other existing varieties of *Dianthus* known to the inventor.

2 Drawing Sheets

Genus: *Dianthus.*
Species: ×*hybrida.*
Denomination: 'WP10 ELE04'.

BACKGROUND OF THE INVENTION

This application claims the benefit of priority under 35 U.S.C. 119(f) of the application for a grant of European Community Plant Breeders Rights which was filed for the instant plant variety on Jun. 25, 2010, Application Number 2010/1269.

The present invention relates to a new and distinct cultivar of hardy *Dianthus,* also known as garden pink, which is grown for use as a flowering plant for pots and containers and for planting in the garden and landscape. The new cultivar is known botanically as *Dianthus×hybrida* and will be referred to hereinafter by the cultivar name 'WP10 ELE04'.

'WP10 ELE04' is a complex hybrid plant that is the product of a long term breeding program conducted by the inventor in a cultivated area of Houndspool, Dawlish, Devon, United Kingdom The inventor selected 'WP10 ELE04' in 2004 for its highly fragrant flowers which are double and light shell pink in color.

'WP10 ELE04' resulted from the controlled pollination between two earlier selections of *Dianthus* from the inventor's breeding program, namely *Dianthus* 'Devon Flavia' (U.S. Plant Pat. No. 15,903) as male parent and Selection "FLA 02.13" (unpatented and unreleased) as female parent.

'WP10 ELE04' is distinguishable from the male parent as follows: Whereas the plant of 'WP10 ELE04' has a compact habit, the habit of the male parent is taller and more vigorous. In addition, the flowers of the male plant are larger, double and light pink in color, with a reddish-purple "eye". The petals of the male parent are more fimbriated than the petals of 'WP10 ELE04'.

'WP10 ELE04' is distinguishable from the female parent as follows: The female plant is taller flowering than 'WP10 ELE04' which has a more compact mounding habit.

The variety of *Dianthus* which is considered by the inventor to most closely resemble 'WP10 ELE04' is the inventor's variety and male parent, *Dianthus* 'Devon Flavia' which is compared above.

Asexual reproduction of 'WP10 ELE04' was first accomplished by the inventor in 2004 in a cultivated area of Houndspool, United Kingdom. The method of asexual propagation used was vegetative cuttings. The inventor has determined that 'WP10 ELE04' is stable and reproduces true to type in successive generations of asexual propagation.

SUMMARY OF THE INVENTION

The following traits have been repeatedly observed and represent the characteristics of the new *Dianthus* cultivar 'WP10 ELE04'. These traits in combination distinguish this cultivar from all other commercial varieties known to the inventor. 'WP10 ELE04' has not been tested under all possible conditions and phenotypic differences may be observed with variations in environmental, climatic and cultural conditions, however, without any variance in genotype.

1. *Dianthus* 'WP10 ELE04' exhibits a compact mounding habit.
2. The flowers of *Dianthus* 'WP10 ELE04' are double.
3. The flowers of *Dianthus* 'WP10 ELE04' are light shell pink in color.
4. *Dianthus* 'WP10 ELE04' blooms from May through October.
5. *Dianthus* 'WP10 ELE04' exhibits glaucous blue-green foliage.
6. At nine months of age, the height of the foliage mound of *Dianthus* 'WP10 ELE04' is 18 cm to 22 cm, and the width is 15 cm to 20 cm.
7. *Dianthus* 'WP10 ELE04' is perennial and is hardy to −15° C.
8. *Dianthus* 'WP10 ELE04' is suitable for use as a flowering plant in pots and containers.

BRIEF DESCRIPTION OF THE DRAWINGS

The accompanying color drawings illustrate the overall appearance of the new *Dianthus* variety 'WP10 ELE04' showing colors as true as it is reasonably possible to obtain in colored reproductions of this type. Colors in the drawings may differ from the color values cited in the detailed botanical description, which accurately describe the actual colors of the new variety 'WP10 ELE04'.

Figure 1:
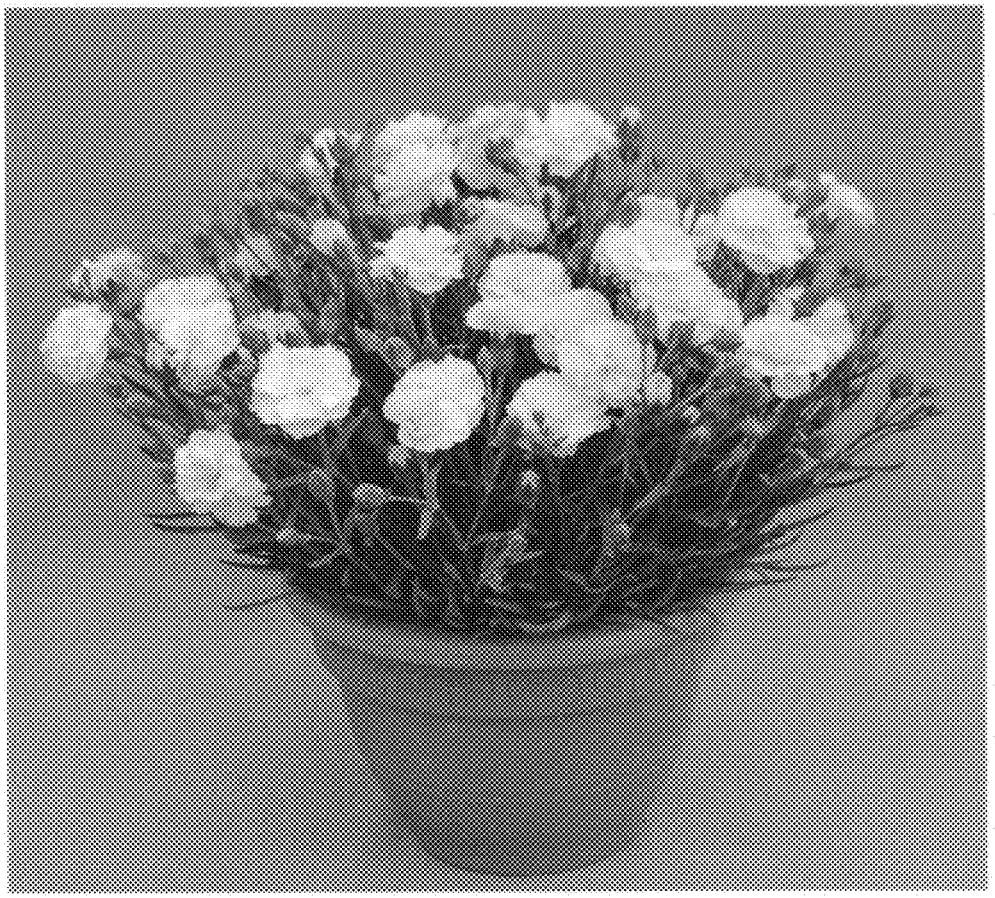

The drawing labeled as FIG. 1 depicts an entire flowering plant of 'WP10 ELE04'.

Figure 2:
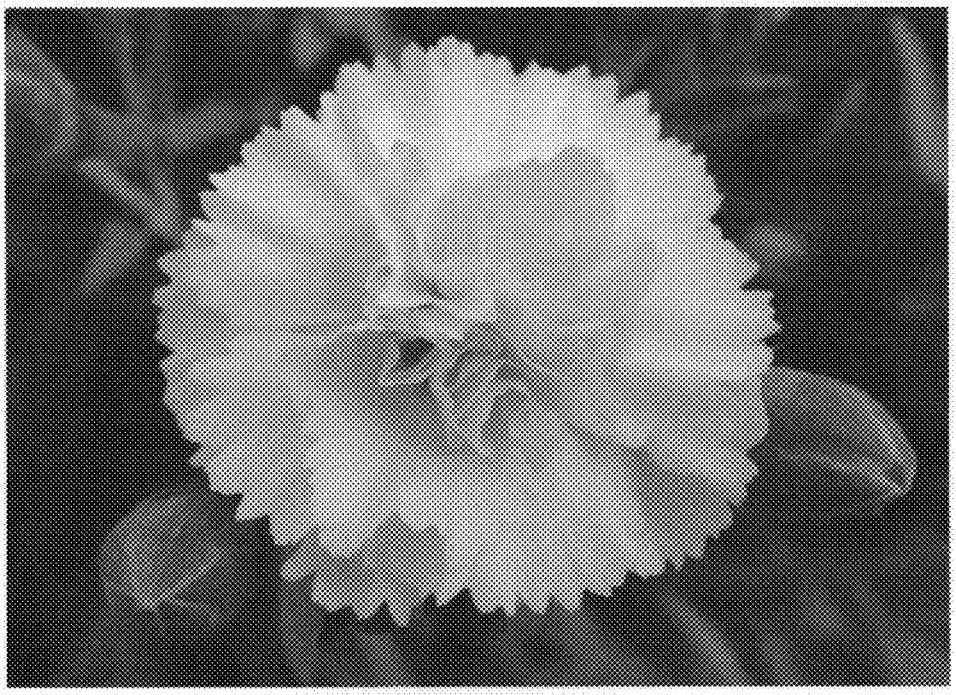

The drawing labeled as FIG. 2 depicts a close-up view of the flower of 'WP10 ELE04'.

All drawings were made from 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP10 ELE04'. Data was collected from 1.5-liter container plants in spring, and grown indoors in Devon, United Kingdom. The color determinations are in accordance with the 2001 edition of the Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
Family: Caryophyllaceae.
Genus: *Dianthus*.
Species: ×*hybrida*.
Denomination: 'WP10 ELE04'.
Parentage: A complex *Dianthus* hybrid that resulted from the open pollination between the following parent plants:
Male parent: *Dianthus* 'Devon Flavia' (U.S. Plant Pat. No. 15,903).
Female parent: Unpatented selection of *Dianthus* from the inventor's breeding program, known as Selection "FLA 02.13".
Plant type: Flowering perennial.
Use of plant: As a flowering plant in containers, window boxes, planters, pots and the garden.
Bloom period: May-October in Devon, UK.
Plant habit: A compact mound with many branches and stems upright.
Height of plant: 18 cm to 22 cm after 9 months.
Width of plant: 15 cm to 20 cm after 9 months.
Hardiness: Has survived in temperatures of minus 15 Centigrade, equivalent to USDA Hardiness Zone 5.
Root system: Many fibrous roots.
Propagation method: Vegetative stem cuttings.
Cultural requirements: Grow in full sun, in well drained and moderately fertile soil, keep well fertilized and watered.
Diseases and pests: No particular resistance or susceptibility to *Dianthus* diseases and pests are known to the inventor.
Temperature for rooting: A minimum of 15° C. air temperature and 21° C. base temperature at root level is required to produce roots on the cuttings.
Time to root cuttings: 10-14 days are required to produce roots on a vegetative cutting using the rooting temperatures above.
Facilities for rooting: Mist propagation unit is required for satisfactory rooting of cuttings.
Crop time (from planting a rooted cutting): 3 months starting in the Spring and 6 months starting in the Fall.
Plant stem:
*Shape.*—Cylindrical.
*Height.*—14 cm to 16 cm.
*Diameter.*—3 mm in diameter.
*Surface.*—Glabrous and glaucous.
*Color.*—188A.
*Branching.*—Numerous shoots from the axils of the lower leaves.
*Internode length.*—From 20 mm (lowest internode) to 55 mm (uppermost internode).
*Node dimensions.*—5 mm in diameter and 3 mm in length.
Leaf:
*Type.*—Evergreen.
*Shape.*—Linear.
*Division.*—Simple.
*Apex.*—Acute.
*Base.*—Decurrent.
*Venation.*—Not prominent.
*Margins.*—Entire.
*Arrangement.*—Opposite and spiraling on stem.
*Attachment.*—Sheathing.
*Surface* (*adaxial and abaxial*).—Glaucous.
*Stipules.*—Absent.
*Fragrance.*—Absent.
*Dimensions.*—Length: 8.5 cm to 9 cm. Width: 4 mm to 5 mm.
*Color.*—Adaxial surface: Ranges between N138A and N138C. Abaxial surface: Ranges between N138A and N138C.
Inflorescence:
*Flower stem.*—Length: 14-16 cm. Width: 3 mm. Stem strength: Erect. Stem color: 188A.
*Inflorescence.*—Cymose.
*Type.*—Salviform, symmetrical.
*Development.*—Singly, in sequence from the uppermost bud.
Buds:
*Shape.*—Cylindrical.
*Dimensions.*—18 mm in length and 9 mm in width.
*Color.*—Ranges between 137C and 137D.
*Surface texture.*—Glabrous.
Flowers:
*Number.*—4 to 5 per stem.
*Pedicel dimensions.*—14 cm-16 cm length and 3 mm in width.
*Pedicel strength.*—Erect.
*Pedicel color.*—188A.
*Flower dimensions.*—Length (including calyx): 36 mm. Diameter: 40 mm.
*Flower shape.*—Circular.
*Flower profile.*—Reflexed.
*Lastingness.*—10 days at 20° C., on the plant.
*Fragrance.*—Moderate, floral.
*Flowering period.*—May to October, in Devon, United Kingdom.
Corolla:
*Shape* (*upper part of corolla*).—Convex.
*Shape* (*lower part of corolla*).—Concave.
*Petal arrangement.*—Persistent, apopetalous, overlapping.

*Petal margin.*—Crenate-dentate.
*Indentation.*—Varies between 0 mm and 1 mm.
*Petal texture.*—Soft.
*Flower type.*—Double.
*Petal number.*—Ranges from 15 to 20.
*Petal dimension.*—Length: 35 mm. Width: 20 mm.
*Color pattern.*—Blade color changes from light pink with thin band of darker pink when fresh, aging to pure white, whiter than N155D.
*Color of surfaces* (*both upper and lower*).—Ground color of blade: 69C. Color of band across blade: 62C. Color of middle of strap: 145C. Color of base of strap: 145C.
*Petal shape.*—Obdeltoid.
*Petal apex.*—Fan shaped.
*Petal base.*—Strap shaped, tapering towards base.
*Petal surface.*—Glabrous.

Calyx:
*Shape.*—Cylindrical, parallel sides.
*Sepal apex.*—Subacute.
*Sepal base.*—Fused.
*Longitudinal profile.*—Flat.
*Dimensions.*—Length: 20 mm. Diameter: 11 mm.
*Sepals.*—Fused to 4-8 mm below the subacute apex.
*Sepals.*—5 in number.
*Sepals color, outer surface.*—Ranges between 137C towards sepal apex, fading to 137D at sepal base.
*Sepals color, inner surface.*—144C.
*Anthocyanin.*—Absent.
*Splitting.*—Not observed.

Epicalyx:
*Bracts number.*—2 arranged as opposite pair.
*Shape.*—Lanceolate; base truncate, apex acute.
*Dimensions.*—Width (at base): 3 mm. Length: 12 mm.
*Color.*—N138A.
*Anthocyanin.*—Absent.

Bracteoles:
*Number.*—1 pair of two.
*Dimensions.*—Width: 10 mm. Length: 12 mm.
*Color.*—N138A.
*Anthocyanin.*—Absent.

Reproductive organs:
*Stamens.*—Absent.
*Pollen.*—Absent.
*Style.*—Number: 2. Shoulder: Absent. Color: White. Length: 20 mm-25 mm. Width: Less than 1 mm.
*Stigma.*—Number: 1 stigma per style. Attachment: Barely discernable, linear, runs along length of style. Dimensions: 20 mm-25 mm; width: less than 0.5 mm. Color: White.
*Ovary.*—Position: Superior. Dimensions: Length: 7 mm. Diameter: 4 mm. Shape: Spindle. Color (upper surface): 145B. Color (lower surface): 145C.
*Seed.*—Seed has not been found during repeated observations.

The invention claimed is:

1. A new and distinct cultivar of *Dianthus* plant named 'WP10 ELE04' as described and illustrated herein.

* * * * *